United States Patent [19]

Kobayashi et al.

[11] Patent Number: 5,190,758
[45] Date of Patent: Mar. 2, 1993

[54] SEBACEOUS EXCITOSECRETORY AGENT

[75] Inventors: Yasunobu Kobayashi; Motonobu Matsumoto, both of Osaka, Japan

[73] Assignee: Sunstar K.K., Osaka, Japan

[21] Appl. No.: 763,707

[22] Filed: Sep. 23, 1991

[30] Foreign Application Priority Data

Sep. 26, 1990 [JP] Japan .................................. 2-258189

[51] Int. Cl.$^5$ ........................ A61K 7/48; A61K 31/19; A61K 47/44; A01N 25/02
[52] U.S. Cl. .................................... 424/401; 514/724; 514/772.1; 514/887; 514/944; 514/969
[58] Field of Search .................. 424/78.03, 401, 78.07; 514/724, 887, 944, 969, 772.1

[56] References Cited

FOREIGN PATENT DOCUMENTS 2934090 3/1981 Fed. Rep. of Germany.

OTHER PUBLICATIONS

Kinsolving et al., "The use of undecylenic acid to treat Herpes labialis", Europ. Pat. Appl., 16 pp. EP 105448A1, (1984) (Abstract only)—chemical abstracts.
Derwent World Patents Index, 351, abstract of DE 2934090.

Primary Examiner—Thurman K. Page
Assistant Examiner—C. Azpuru
Attorney, Agent, or Firm—Sughrue, Mion, Zinn, Macpeak & Seas

[57] ABSTRACT

A sebaceous excitosecretory agent comprising at least one of undecylenic acid, its salts, its esters, and its amide derivatives as an active ingredient. A process for exciting secretion of sebum comprising the step of applying onto a skin surface the above sebaceous excitosecretory agent. The sebaceous excitosecretory agent has a long-lasting action to excite secretion of sebum.

5 Claims, No Drawings

SEBACEOUS EXCITOSECRETORY AGENT

FIELD OF THE INVENTION

The present invention relates to a sebaceous excitosecretory agent exhibiting a long-lasting excitosecretory action on sebaceous glands.

BACKGROUND OF THE INVENTION

The skin or hair is kept healthy and beautiful by sebum secreted from sebaceous glands. However, the skin gradually loses its smoothness and moistness from adolescence to senescence due to a failure of the sebaceous secretory function, especially in females. For the purpose of supplying oily matters to the skin suffering from a failure of sebaceous secretory function, drugs, medical supplies and cosmetics for oil supply in various forms such as creams, clear lotions and milky lotions, have hitherto been employed.

When conventional products for oil supply are applied to the skin, oily components are of short duration due to gradual removal by external causes such as rubbing although temporarily retained on the skin surface.

SUMMARY OF THE INVENTION

An object of the present invention is to provide a sebaceous excitosecretory agent that has a prolonged action of exciting secretion of sebum and continuously accelerates oil supply to the skin.

Another object of the present invention is to provide a process for exciting secretion of sebum using the above sebaceous excitosecretory agent.

Other objects and effects of the present invention will be apparent from the following description.

The inventors of the present invention have studied various physiologically active substances and found as a result that undecylenic acid excites the function of sebaceous glands and thus completed the present invention.

The present invention relates to a sebaceous excitosecretory agent comprising at least one of undecylenic acid, its salts, its esters, and its amide derivatives as an active ingredient.

The present invention also relates to a process for exiting secretion of sebum comprising the step of applying the above sebaceous excitosecretory agent onto a skin surface.

DETAILED DESCRIPTION OF THE INVENTION

Incorporation of the above-described active ingredient(s) into products for oil supply affords a sebaceous excitosecretory agent having an excitative effect on the sebum secretory function essentially possessed by the human skin as well as the conventional function of oil supply thereby making it possible to supply oily matters to the skin in a natural mode and in a continuous manner.

The sebaceous excitosecretory agent of the present invention also proved effective to improve the skin in the convalescence following senile xeroderma and eszematosis of dry type such as atopic dermatitis.

Undecylenic acid is a fatty acid present in sweat and is known for long to have antimicrobial activity. There has been reported that undecylenic acid is incorporated into shampoos, etc. as an anti-dandruff agent or used as not yet been reported.

Undecylenic acid to be used in the present invention may be in the form of a free acid as well as a salt, an ester or an amide derivative. Examples of the salts of undecylenic acid include potassium, sodium, calcium, magnesium, and zinc salts. Examples of the undecylenic esters include alkyl esters, e.g., methyl, ethyl, propyl, and isopropyl esters; aromatic esters, e.g., benzyl and allyl esters; esters with a polyhydric alcohols, e.g., glycerin, propylene glycol, and polyethylene glycol; and an epoxypropyl ester. Examples of the amide derivatives of undecylenic acid include a monoethanolamide and a diethanolamide. However, the salt, ester or amide derivative of undecylenic acid used in the present invention is not limited to the above examples. The undecylenic acid and derivatives thereof may be used either individually or in combination of two or more thereof.

The sebaceous excitosecretory action of undecylenic acid was investigated according to the following Reference Example.

REFERENCE EXAMPLE

Ten week-old hamsters were divided into three groups each consisting of 4 animals. A first group was maintained on 0.05 ml/animal/day of a 5 wt % solution of undecylenic acid in ethanol applied to the inner side of the auricle for consecutive 14 days. A second group was maintained on 0.05 ml/animal/day of a 1 wt % solution of undecylenic acid in ethanol in the same manner. To a third group (control), ethanol containing no undecylenic acid was administered in the same manner. After 14-day administration, the area of the sebaceous glands in the inner side of the auricle was measured by means of an image analyzer. The results obtained are shown in Table 1 below.

TABLE 1

| Group | Undecylenic Acid Concentration (wt %) | Number of Animals | Total Area of 100 Sebaceous Glands (mm$^2$) |
|---|---|---|---|
| 1st Group | 5 | 4 | 4.31 ± 1.00 |
| 2nd Group | 1 | 4 | 2.56 ± 0.42 |
| Control | 0 | 4 | 1.92 ± 0.18 |

As is apparent from Table 1, undecylenic acid increases sebaceous glands of the auricle in size.

Components of the sebaceous excitosecretory agent other than the above-mentioned active ingredients can be selected from known components.

The sebaceous excitosecretory agent of the present invention may have various dose forms, such as clear lotions, oils, ointments, creams, and milky lotions, according to known techniques.

Undecylenic acid is a fatty acid contained in sweat as stated above and is of no harm to the human body. Therefore, the concentrations of undecylenic acid, its salts, its ester derivatives, and its amide derivatives in these dose forms is not particularly limited and can appropriately be determined according to the dose form as long as the effectiveness of the agent is not adversely affected. The concentration is generally from 0.01 to 10% by weight, and preferably from 0.1 to 5% by weight, based on the total amount of the agent.

If desired, the sebaceous excitosecretory agent of the present invention may further contain other components generally employed in conventional cosmetics as long as the effects of the present invention are not impaired.

The conventional components and its production process as well as the conventional components added thereto of the cosmetic compositions are described, e.g., in *Keshohin-Gaku* (Cosmetic Science), edited by T. Ikeda, published on May 20, 1979 by Nanzando, Japan, which is incorporated herein by reference, but the present invention is not construed as being limited thereto. Related portions of this reference are shown in the following table.

| Cosmetics | Compositions and production process | Other components |
|---|---|---|
| Lotions | page 220, line 14 to page 221, line 12 up | page 251, Table 31 |
| Creams | page 235, line 9 up to page 236, line 6 up | page 227, line 6 up to page 228, line 5 |
| Emulsions | page 243, line 10 to page 244 | page 242, line 12 to line 6 up |

The sebaceous excitosecretory agent of the present invention can be used in a conventional manner so as to excite secretion of sebum to prevent drying of the skin. For example, the sebaceous excitosecretory agent of the present invention can be applied to dry parts of the skin surface with hands or fingers one or more times a day for the face, or 2 to 4 times a day for hands, legs and other parts. The application amount of the sebaceous excitosecretory agent of the present invention varies depending on the composition and the part to which the agent is applied, and is generally from 0.05 to 1.0 g per 100 cm$^2$ of skin.

The present invention is now illustrated in greater detail by way of Formulation Examples and Test Example, but it should be understood that the present invention is not deemed to be limited thereto. All the percents are by weight unless otherwise indicated.

FORMULATION EXAMPLE 1
Clear Lotion

| | |
|---|---|
| Zinc undecylenate | 0.5% |
| 1,3-Butylene glycol | 6.0% |
| Ethanol | 8.0% |
| Polyoxyethylene hydrogenated castor oil (60 E.O.) | 0.8% |
| Methyl p-hydroxybenzoate | 0.05% |
| Citric acid | 0.05% |
| Sodium citrate | 0.07% |
| Perfume | 0.1% |
| Purified water | balance |
| | 100% in total |

The clear lotion having the above formulation can be used by applying with hands to a dry skin surface of a face, hands, leg and the like several times a day.

FORMULATION EXAMPLE 2
Oil

| | |
|---|---|
| Ethyl undecylenate | 0.5% |
| Cholesteryl stearate | 1.0% |
| Olive oil | 2.0% |
| Squalane | balance |
| | 100% in total |

The oil having the above formulation can be used by applying a few drops of the oil to a dry skin surface of a face, hands, legs and the like 1 to several times a day.

FORMULATION EXAMPLE 3
Cream

| | |
|---|---|
| Undecylenic acid | 1.0% |
| Bleached bees wax | 4.0% |
| Cetanol | 2.0% |
| Lanoline | 2.0% |
| Liquid paraffin | 9.0% |
| Self-emulsifiable glycerol monostearate | 3.0% |
| Polyoxyethylene sorbitan monostearate (20 E.O.) | 1.5% |
| Propyl p-hydroxybenzoate | 0.1% |
| Methyl p-hydroxybenzoate | 0.2% |
| 1,3-Butylene glycol | 5.0% |
| Perfume | 0.2% |
| Purified water | balance |
| | 100% in total |

The cream having the above formulation can be used by applying to a dry skin surface of a face, hands, legs and the like 1 to 3 times a day.

FORMULATION EXAMPLE 4
Milky Lotion

| | |
|---|---|
| Undecylenic acid monoethanolamide | 1.0% |
| Liquid paraffin | 5.0% |
| Vaseline | 2.0% |
| Bees wax | 1.0% |
| Sorbitan sesquioleate | 2.0% |
| Polyoxyethylene oleyl ether (20 E.O.) | 2.5% |
| Ethyl p-hydroxybenzoate | 0.2% |
| 1,3-Butylene glycol | 5.0% |
| Carboxyvinyl polymer | 0.5% |
| Potassium hydroxide | 0.3% |
| Perfume | 0.2% |
| Purified water | balance |
| | 100% in total |

The milky lotion having the above formulation can be used by applying in the similar manner as for the clear lotion.

TEST EXAMPLE

Twenty females ranging in age from 39 to 53 were divided into two groups (10 females per group). 0.1 ml of the cream prepared in Formulation Example 3 was applied to the forehead of a first group once a day for 4 weeks. A control cream having the same composition as the cream except for containing no undecylenic acid was applied to the forehead of a second group in the same manner. After 4 weeks, the applied part was washed with a face cleaner. After standing for 2 hours, cigarette paper (2×3 cm) was attached to the part for 3 hours to collect the sebum secreted on the skin surface. The sebum was extracted from the cigarette paper and weighed. The results obtained are shown in Table 2 below.

TABLE 2

| Group | Amount of Sebum (mg/cm$^2$/3 hr) |
|---|---|
| 1st Group | 0.24 ± 0.06 |
| Control | 0.19 ± 0.05 |

As can be seen from Table 2, the test group maintained on the cream containing undecylenic acid revealed a significant increase of sebum on the surface of the skin.

As described and demonstrated above, the cosmetics for skin care according to the present invention excite the sebaceous secretory function essentially possessed by the human skin and supply oily matters to the skin in a natural and continuous manner to thereby give the skin or hair smoothness and moistness. Further, the sebaceous excitosecretory agent of the present invention is effective to improve skin conditions in the convalescence eszematosis of dry type such as senile xeroderma and atopic dermatitis.

While the invention has been described in detail and with reference to specific examples thereof, it will be apparent to one skilled in the art that various changes and modifications can be made therein without departing from the spirit and scope thereof.

What is claimed is:

1. A process for exciting secretion of sebum comprising the step of applying onto a skin surface a sebaceous excitosecretory agent comprising at least one of undecylenic acid, its salts, its esters, and its amide derivatives as an active ingredient, wherein the concentration of said at least one of undecylenic acid, its salts, its esters, and its amide derivatives is from 0.01 to 10% by weight based on the total amount of said agent.

2. A process for exciting secretion of sebum as claimed in claim 1, wherein said salts of undecylenic acid are selected from the group consisting of potassium, sodium, calcium, magnesium, and zinc; said esters of undecylenic acid are selected from the group consisting of alkyl esters, aromatic esters, polyhydric alcohol esters, and an epoxypropyl ester; and said amide derivatives of undecylenic acid are selected from the group consisting of monoethanolamide and diethanolamide.

3. A process for exciting secretion of sebum as claimed in claim 2, wherein said alkyl esters of undecylenic acid are selected from the group consisting of methyl, ethyl, propyl, and isopropyl esters; said aromatic esters of undecylenic acid are selected from the group consisting of benzyl and allyl esters; and, said polyhydric alcohol esters of undecylenic acid are selected from the group consisting of glycerin, propylene glycol, and polyethylene glycol.

4. A process for exciting secretion of sebum as claimed in claim 1, wherein the concentration of said at least one of undecylenic acid, its salts, its esters, and its amide derivatives is from 0.1 to 5% by weight based on the total amount of said agent.

5. A process for exciting secretion of sebum as claimed in claim 1, wherein said agent is in the dose form of a clear lotion, an oil, an ointment, a cream or a milky lotion.

* * * * *